United States Patent [19]

Baba

[11] 4,401,123
[45] Aug. 30, 1983

[54] ENDOSCOPE HAVING AN ULTRASONIC DIAGNOSIS FUNCTION

[75] Inventor: Kazuo Baba, Hachioji, Japan

[73] Assignee: Olympus Optical Co., Ltd., Tokyo, Japan

[21] Appl. No.: 260,298

[22] Filed: May 4, 1981

[30] Foreign Application Priority Data

May 9, 1980 [JP] Japan .................................. 55-61346

[51] Int. Cl.³ .......................... A61B 1/06; A61B 10/00
[52] U.S. Cl. ......................................... 128/660; 128/6
[58] Field of Search ............................... 128/660, 6-8, 128/4, 303.15

[56] References Cited

U.S. PATENT DOCUMENTS

| 2,079,233 | 5/1937 | Wappler ................................. 128/7 |
| 4,008,603 | 2/1977 | Paulissen . |
| 4,273,111 | 6/1981 | Tsukaya ........................... 128/660 X |
| 4,327,738 | 5/1982 | Green et al. ......................... 128/6 X |

FOREIGN PATENT DOCUMENTS 54-1984  1/1979  Japan ..................................... 128/660

Primary Examiner—Kyle L. Howell
Assistant Examiner—John C. Hanley
Attorney, Agent, or Firm—Frishauf, Holtz, Goodman & Woodward

[57] ABSTRACT

An endoscope having an ultrasonic diagnosis function, comprises a distal end including an observing portion connected to a flexible tube, and provided with a view window and an illumination window formed on one surface thereof; an ultrasonic wave emitting-receiving portion located on the tip side of the observing portion aligned with the observing portion and provided with an ultrasonic oscillator having an ultrasonic wave emitting and receiving plane parallel with the view window; and a parallel moving link mechanism for moving the ultrasonic wave emitting-receiving portion such that it is moved away from the observing portion with the ultrasonic wave emitting-receiving plane kept substantially parallel with the view window.

11 Claims, 6 Drawing Figures

ENDOSCOPE HAVING AN ULTRASONIC DIAGNOSIS FUNCTION

BACKGROUND OF THE INVENTION

This invention relates to an endoscope provided with an ultrasonic oscillation unit having a plane for emitting and receiving an ultrasonic wave so as to perform an ultrasonic diagnosis.

A conventional endoscope, shown in FIG. 1, capable of performing an ultrasonic diagnosis comprises, for example, an electron scanning type ultrasonic oscillator 5 disposed at the distal end 2 of the insertion portion 1, i.e., the portion inserted into the body cavity. The oscillator comprises a plane for emitting and receiving an ultrasonic wave, said plane being located on the same side as a view window 3 and an illumination window 4 provided on the distal end 2 of the endoscope. For performing an ultrasonic diagnosis, the distal end 2 is bent while a body cavity wall 6 is being observed through the view window 3 so as to bring the ultrasonic wave emitting-receiving plane of the ultrasonic oscillator 5 into direct contact with the desired portion of the body cavity wall 6.

In the prior art endoscope of this type, however, the view window 3 is also moved together with the ultrasonic oscillator 5. Thus, it is impossible to secure a sufficient view field, rendering it difficult to bring the wave emitting-receiving plane of the oscillator 5 accurately to the desired position. Also, the manual operation for bringing the wave emitting-receiving plane into direct contact with the desired portion of the body cavity wall 6 requires a skill of high level; in general, it is difficult to achieve a satisfactory contact in question. Further, the illumination window 4 is also moved together with the view window 3, quite naturally. Thus, if light of high intensity is used for illumination purposes, the body cavity wall 6 tends to be burned. In order to avoid a accident, it is necessary to use a weak illumination light, making the manual operation of the endoscope more difficult.

An object of this invention is to provide an endoscope easy to operate and permitting the ultrasonic wave emitting-receiving plane of an ultrasonic oscillator to be brought accurately to the desired position.

SUMMARY OF THE INVENTION

According to the present invention, an endoscope having an ultrasonic diagnosis function, comprises a control section for controlling operations of the endoscope; a distal end; and a flexible tube connecting the control section to the distal end. The distal end includes an observing portion coupled to the flexible tube, the observing portion having a first axis, and being provided with a view window and an illumination window formed on one surface thereof substantially in parallel with the first axis; an ultrasonic wave emitting-receiving portion located adjacent to the observing portion and having a second axis substantially in parallel with and selectively aligned with the first axis and provided with an ultrasonic oscillator having an ultrasonic wave emitting and receiving plane substantially in parallel with the view window and the second axis; and a mechanism coupled to the observing portion and to the ultrasonic wave emitting-receiving portion for moving the ultrasonic wave emitting-receiving portion relative to the observing portion such that the second axis is moved away from but substantially in parallel with the first axis and for keeping the ultrasonic wave emitting-receiving plane substantially parallel with the view window.

This invention can be more fully understood from the following detailed description when taken in conjunction with the accompanying drawings.

BRIEF DESCRIPTION OF THE DRAWINGS

FIGS. 2 to 6 collectively show an endoscope according to one embodiment of this invention, wherein FIG. 2 is a side view of the entire endoscope, FIG. 3 is a side view showing the insertion portion of the endoscope, which is inserted into a body cavity, FIG. 4 is a plan view showing the insertion portion shown in FIG. 3, FIG. 5 is a cross sectional view along line V—V of FIG. 4, and FIG. 6 is a side view showing how the insertion portion is operated within a body cavity.

DETAILED DESCRIPTION

Figure 1:
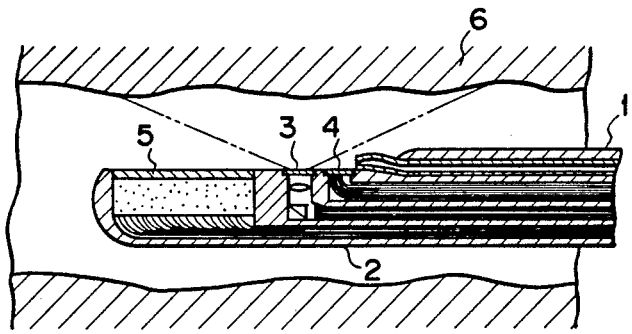
FIG. 1 is a cross sectional view schematically showing a prior art endoscope whose distal end portion is inserted into a body cavity.
Figure 2:
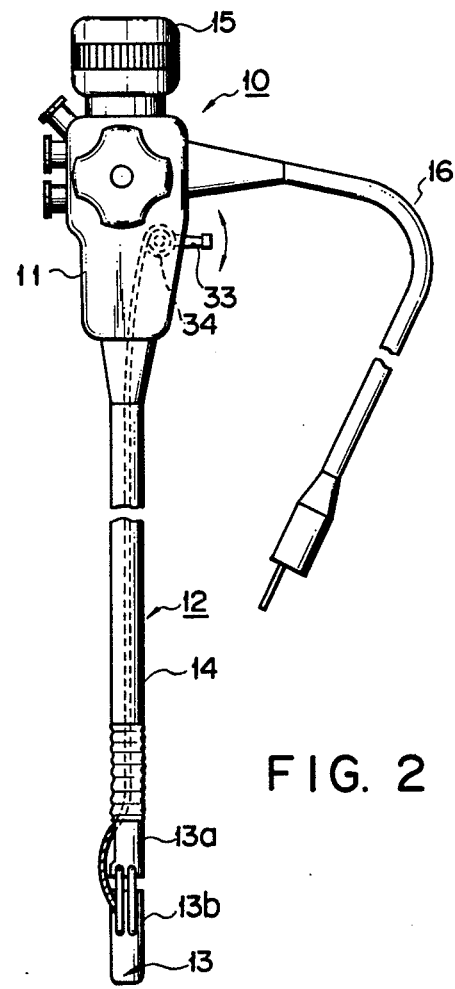

FIG. 2 shows a side view of an endoscope 10 according to one embodiment of this invention. The endoscope 10 comprises a control section 11 and an insertion section 12. The insertion section 12 includes a distal end 13 and a flexible tube 14 connecting the control section 11 and the distal end 13. The control section 11 is provided with an eyepiece portion 15 and a universal cord 16 connected to a light source device (not shown). Further, the distal end 13 includes an observing portion 13a located on the side of the flexible tube 14 and extending along a first axis, and an ultrasonic wave emitting-receiving portion 13b located on the tip side and extending along a second axis.

Figure 3:
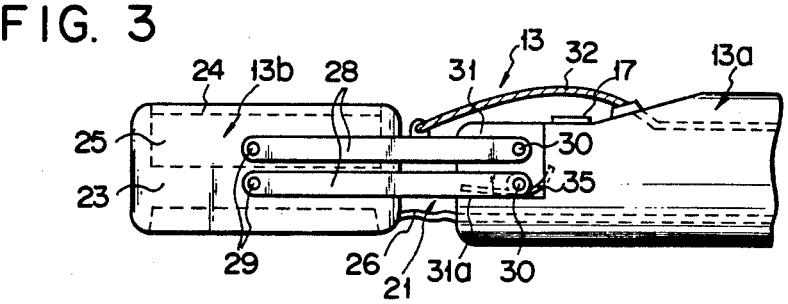
Figure 4:
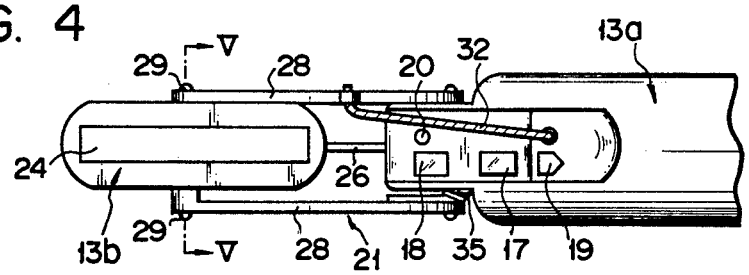
Figure 5:
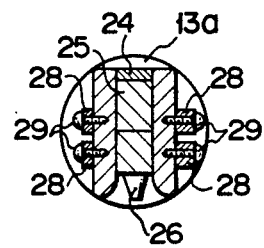

As shown in FIGS. 3 and 4, the observing portion 13a is provided on one side with a view window 17 of an observing optical system, said view window 17 being parallel with the first axis mentioned previously, an illumination window 18 of an illuminating optical system, a nozzle 19 for injecting air and water, and a suction port 20. The observing optical system is constructed to permit observing the view field of the window 17 from the eyepiece portion 15 through the window 17. Also, the illuminating optical system is constructed to allow the view field of window 17 to be illuminated through the window 18 by the light introduced via the universal cord 16. Incidentally, each of these optical systems is well known in this technical field.

Figure 6:
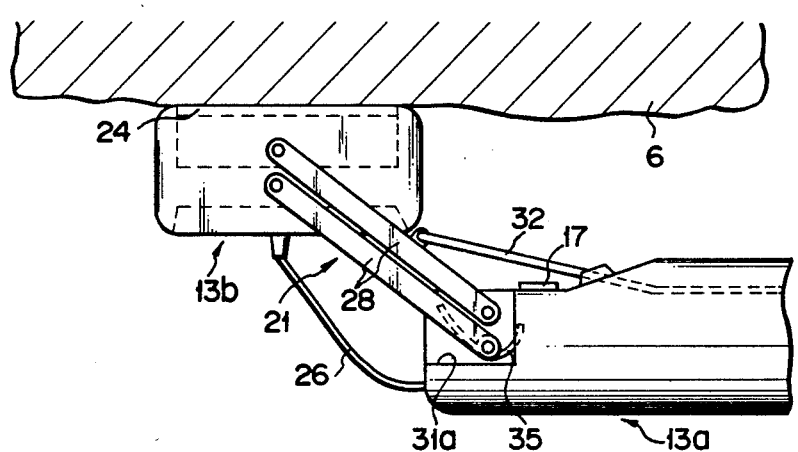

The ultrasonic wave emitting-receiving portion 13b is formed separately from the observing portion 13a and located normally such that the first axis mentioned previously is aligned with the second axis mentioned previously. As seen from, particularly, FIG. 6, these portions 13a and 13b are joined to each other by two pairs of links 28 so as to form a parallel moving link mechanism 21. The portion 13b is provided with an ultrasonic oscillation unit of known type having a base body 23, an electron scanning type ultrasonic oscillator 24, a damper 25, and a signal cable 26. The oscillator 24 is disposed such that the plane for emitting and receiving an ultrasonic wave faces the view field of the view window 17. For allowing the particular plane of the oscillator 24 to face the view field of the window 17, substantially coplanar flat surfaces are formed on the observing portion 13a and the ultrasonic wave emitting-receiving portion 13b on the same side. The view window 17 and the ultrasonic wave emitting-receiving plane are located on the coplanar surfaces.

The signal cable 26 is connected at one end to the ultrasonic oscillator 24 and extends into the operating portion 15 through the portion 13b and the flexible tube 14 so as to be connected at the other end to an ultrasonic wave emitting-receiving circuit (not shown) provided outside the body of the endoscope. In general, the other end of the signal cable 26 is connected to the circuit mentioned above via the universal cord 16. Also, the signal cable 26 is covered with an acid-resisting material at the exposed region between the observing portion 13a and the ultrasonic wave emitting-receiving portion 13b for protection of the exposed portion.

The parallel moving link mechanism 21 is very important in this invention. Specifically, the four links 28 forming two pairs are the same in length and the two pairs of the links 28 are mounted to the opposite side planes of the distal end 13. Incidentally, the opposite side planes mentioned are substantially perpendicular to the coplanar planes of the distal end 13, i.e., the flat surfaces on which are located the view window 17 and the ultrasonic wave emitting-receiving plane. As seen from FIG. 3, the paired links 28 are vertically apart from and parallel with each other, and each link 28 is pivoted at one end to the side plane of the portion 13b by a pin 29 and at the other end to the side plane of the portion 13a by a pin 30. Thus, the links 28 permit moving the ultrasonic wave emitting-receiving portion 13b from the stationary position shown in FIG. 3 to the operable position shown in FIG. 6, with the ultrasonic wave emitting-receiving plane of the portion 13b kept parallel with the view window 17 of the observing portion 13a. A recess 31 is formed in the upper tip portion of each of the side planes of the observing portion 13a and the pins 30 are fixed to the recess 31. The lower plane of the lower link 28 abuts against a flat bottom plane 31a of the recess 31 under the normal condition so as to keep the ultrasonic wave emitting-receiving portion 13b substantially aligned with the observing portion 13a as shown in FIG. 3.

An operating wave 32 serving to operate the ultrasonic wave emitting-receiving portion 13b is connected at one end to the central portion of the link 28 and extends through the observing portion 13a and the flexible tube 12 so as to be wound at the other end portion around a pulley 34 rotatably mounted to the control section 11 as shown in FIG. 2. The pulley 34 is connected via, for example, a gear mechanism to an operation knob 33 rotatably mounted to the control section 11 and having the tip portion extending from the control section 11. The knob 33 is rotatable in the direction denoted by arrows in the drawing and the rotation of the knob 33 is transmitted to the pulley 34 by, for example, the gear mechanism mentioned above. Further, a leaf spring 35 is provided such that one end thereof is fixed to the observing portion 13a, with the other end being engaged with the link 28. As seen from FIG. 6, the leaf spring 35 serves to urge the ultrasonic wave emitting-receiving portion 13b in the counterclockwise direction, namely, from the operative position to the rest position.

In operating the endoscope of the particular construction described above, the distal end 13 is inserted into a body cavity of a patient and brought to the region near the desired portion. Then, the distal end 13 is brought to the desired portion while the body cavity is observed through the view window 17 by utilizing the light emitted through the illumination window 18. Under this condition, the body cavity wall 6 is observed and the knob 33 is operated so as to pull the wire 32. In the process of pulling the wire 32, the ultrasonic wave emitting-receiving portion 13b is moved gradually via the link mechanism 21, with the ultrasonic wave emitting-receiving plane of the portion 13b kept parallel with the view window 17 as seen from FIG. 6. Finally, the above-mentioned plane of the portion 13b is brought into direct contact with the body cavity wall 6. Then, the oscillator 24 is actuated by the ultrasonic wave emitting-receiving circuit so as to emit an ultrasonic wave toward the body cavity wall 6 and to receive the wave reflected by the body cavity wall 6. In this fashion, the ultrasasonic wave is scanned for detecting a diseased portion, if any, in the body cavity wall. After completion of the diagnosis, the knob 33 is operated again so as to loosen the operating wire 32. As a result, the leaf spring 35 permits the ultrasonic wave emitting-receiving portion 13b to be brought back to the rest position aligned with the observing portion 13a as shown in FIG. 3. Finally, the distal end 13 is withdrawn from the body cavity.

It is important to note that the ultrasonic wave emitting-receiving portion 13b is moved in substantially parallel with the observing portion 13a so as to be brought into direct contact with the body cavity wall 6 as described previously. Thus, a clearance large enough to ensure observation of the body cavity wall 6 is provided between the view window 17 of the observing portion 13a and the body cavity wall 6 to be examined. It follows that a skill of high level is not required for bringing the ultrasonic wave emitting-receiving plane of the portion 13b into direct contact with the desired portion of the body cavity wall 6 without fail. Further, the diagnosis can be performed with the illumination window 18 of the observing portion 13a kept sufficiently apart from the body cavity wall 6, rendering it substantially impossible for the body cavity wall to be burned.

In the embodiment described above, a system constructed by a parallel moving link mechanism and an operation knob connected to the link mechanism is used for moving the ultrasonic wave emitting-receiving plane of the portion 13b in substantially parallel with the view window 17 of the observing portion 13a. But, the parallel moving mechanism need not be restricted to the system mentioned above. For example, a pantograph mechanism through which the ultrasonic wave emitting-receiving portion is supported by the observing portion may be used for achieving the parallel movement of the wave emitting-receiving portion.

What is claimed is:

1. An endoscope having an ultrasonic diagnosis function, comprising:
a control section for controlling operations of the endoscope;
a distal end; and
a flexible tube connecting said control section and said distal end; said distal end including:
an observing portion coupled to said flexible tube, said observing portion having a first axis, and being provided with a view window and an illumination window formed on one surface thereof substantially in parallel with said first axis;

an ultrasonic wave emitting-receiving portion located adjacent to said observing portion and having a second axis substantially in parallel with and selectively aligned with said first axis and provided with an ultrasonic oscillator having an ultrasonic wave emitting and receiving plane substantially in parallel with said view window and said second axis; and a mechanism coupled to said observing portion and to said ultrasonic wave emitting-receiving portion for moving said ultrasonic wave emitting-receiving portion relative to said observing portion such that said second axis is moved away from but substantially in parallel with said first axis and for keeping said ultrasonic wave emitting-receiving plane substantially parallel with said view window.

2. The endoscope according to claim 1, wherein said mechanism for moving said ultrasonic wave emitting-receiving portion relative to said observing portion comprises:

a plurality of links coupling said ultrasonic wave emitting-receiving portion to said observing portion; and an operating member mounted to said control section and being coupled to said links for driving said links to move said portions relative to each other.

3. The endoscope according to claim 2, wherein said plurality of links comprises a pair of substantially parallel links, each link being pivoted at the respective end thereof to said observing portion and to said ultrasonic wave emitting-receiving portion, respectively, so that said links remain substantially parallel with each other during movement of said links, said links comprising a parallel moving link mechanism.

4. The endoscope according to claim 2, wherein said observing portion and said ultrasonic portion have sides, and wherein said plurality of links comprise two pairs of links, each of the links forming each pair being pivoted to the side of each of said observing portion and said ultrasonic wave emitting-receiving portion.

5. The endoscope according to claim 4, wherein said sides of said observing portion and of said ultrasonic portion comprise respective opposed side planes.

6. The endoscope according to claim 4 or 5, wherein said sides are substantially perpendicular to said ultrasonic wave emitting and receiving plane and to said view window.

7. The endoscope according to claim 3 or 4, wherein said observing portion has a tip end portion which is provided with at least one abutment means against which a respective one of said links abuts to maintain said ultrasonic wave emitting-receiving portion at a position at which said second axis is substantially aligned with said first axis.

8. The endoscope according to claim 7, wherein said abutment means comprises a substantially smooth surface on said tip end portion of said observing portion.

9. The endoscope according to claim 7, further comprising a spring link to abut against said abutment means.

10. The endoscope according to claim 9, wherein said abutment means comprises a substantially smooth surface on said tip end portion of said observing portion.

11. The endoscope according to claim 1, wherein said moving mechanism comprises operating means mounted to said control section for operatively controlling said moving mechanism.

* * * * *